US007763590B2

(12) United States Patent
Kreutzer et al.

(10) Patent No.: US 7,763,590 B2
(45) Date of Patent: Jul. 27, 2010

(54) COMPOSITIONS AND METHODS FOR INHIBITING EXPRESSION OF A MUTANT GENE

(75) Inventors: Roland Kreutzer, Weidenberg (DE);
Stefan Limmer, Neudrossenfeld (DE);
Matthias John, Hallstadt (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 150 days.

(21) Appl. No.: 10/384,463

(22) Filed: Mar. 7, 2003

(65) Prior Publication Data

US 2005/0074757 A1  Apr. 7, 2005

Related U.S. Application Data

(63) Continuation-in-part of application No. PCT/EP02/11969, filed on Oct. 25, 2002.

(30) Foreign Application Priority Data

| Oct. 26, 2001 | (DE) | ................................. 101 55 280 |
| Nov. 29, 2001 | (DE) | ................................. 101 58 411 |
| Dec. 7, 2001 | (DE) | ................................. 101 60 151 |
| Aug. 2, 2002 | (DE) | ................................. 102 35 620 |

(51) Int. Cl.
*A61K 48/00* (2006.01)
(52) U.S. Cl. .................... 514/44; 536/24.5; 536/24.31; 536/24.1
(58) Field of Classification Search ................ 435/6, 435/91.1, 91.3, 325, 375; 536/23.1, 24.5, 536/24.3, 24.31, 24.33; 514/44
See application file for complete search history.

(56) References Cited

U.S. PATENT DOCUMENTS

| 6,423,489 B1 | 7/2002 | Anderson et al. |
| 6,486,299 B1 | 11/2002 | Shimkets |
| 6,506,559 B1 * | 1/2003 | Fire et al. ....................... 435/6 |
| 2002/0086356 A1 * | 7/2002 | Tuschl et al. ................ 435/69.1 |
| 2002/0114784 A1 | 8/2002 | Li et al. |
| 2002/0123034 A1 | 9/2002 | Canaani et al. |
| 2002/0132346 A1 | 9/2002 | Cibelli |
| 2002/0162126 A1 | 10/2002 | Beach et al. |
| 2002/0173478 A1 | 11/2002 | Gewirtz |
| 2003/0027783 A1 | 2/2003 | Zernicka-Goetz et al. |
| 2003/0108923 A1 | 6/2003 | Tuschl et al. |
| 2003/0125281 A1 | 7/2003 | Lewis et al. |
| 2003/0143732 A1 | 7/2003 | Fosnaugh et al. |
| 2003/0148341 A1 | 8/2003 | Sin et al. |
| 2003/0157030 A1 | 8/2003 | Davis et al. |
| 2003/0176671 A1 | 9/2003 | Reed et al. |
| 2003/0180756 A1 | 9/2003 | Shi et al. |
| 2003/0190635 A1 | 10/2003 | McSwiggen |
| 2003/0198627 A1 | 10/2003 | Arts et al. |
| 2004/0192629 A1 * | 9/2004 | Xu et al. .................... 514/44 |
| 2004/0259247 A1 * | 12/2004 | Tuschl et al. ................ 435/375 |

FOREIGN PATENT DOCUMENTS

| DE | 199 03 713 | 1/1999 |
| DE | 199 56 568 | 11/1999 |
| DE | 20023125 U1 | 1/2000 |
| DE | 10100588 | 1/2001 |
| DE | 10163098 | 12/2001 |
| DE | 101 00 586 | 4/2002 |
| DE | 10230996 | 7/2002 |
| DE | 10230997 | 7/2002 |
| DE | 102 35 620.3 | 8/2002 |
| EP | 1214945 A2 | 1/2000 |
| WO | WO 94/01550 * | 7/1994 |
| WO | WO 99/32619 | 7/1999 |
| WO | WO 99/53050 | 10/1999 |
| WO | WO 99/61631 | 12/1999 |
| WO | WO 00/01846 | 1/2000 |
| WO | WO 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |

(Continued)

OTHER PUBLICATIONS

Holen et al. Positional effects of short interfering RNAs targeting the human coagulation trigger Tissue Factor. Nucleic Acids Research, 202, vol. 30, No. 8: 1757-1766. Oxford University Press.*

(Continued)

*Primary Examiner*—Kimberly Chong
(74) *Attorney, Agent, or Firm*—Fenwick & West LLP (57) ABSTRACT

The present invention relates to a double-stranded ribonucleic acid (dsRNA) for inhibiting the expression of a mutant gene, comprising a complementary RNA strand having a complementary region that is substantially complementary to a portion of the mutant gene, and which is partially complementary to the corresponding wild-type gene. The invention further relates to a pharmaceutical composition comprising the dsRNA and a pharmaceutically acceptable carrier. The pharmaceutical compositions are useful for inhibiting the expression of a target mutant gene, as well as for treating diseases caused by expression of the target gene. The invention also relates to methods for inhibiting the expression of a target mutant gene, as well as methods for treating diseases caused by the expression of the target gene.

7 Claims, 2 Drawing Sheets

FOREIGN PATENT DOCUMENTS

| | | |
|---|---|---|
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A2 | 2/2002 |
| WO | WO 02/26780 A2 | 4/2002 |
| WO | WO 02/44321 * | 6/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A2 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A2 | 2/2003 |
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/040366 A | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |

OTHER PUBLICATIONS

Martinez et al. Synthetic small inhibiting RNAs: Efficient tools to inactivate oncogenic mutations and restore p53 pathways. PNAS, 2002, vol. 99, No. 23: 14849-14854. National Academy of Sciences.*

Ten Asbroek et al. Polymorphisms in the large subunit of human RNA polymerase II as target for allele-specific inhibition. Nucleic Acids Research 2000, vol. 28. No. 5: 1133-1138.*

Holen, T. et al., (2002), "Positional effects of short interfering RNAs targeting the human coagulation trigger Tissue Factor", *Nucleic Acids Research*, 30(8):1757-1766.

Ambros, V., (2001), "Dicing Up RNAs", *Science*, 293:811-813.

Elbashir, S.M. et al., (2001), "Duplexes of 21-nucleotide RNAs mediate RNA interference in cultured mammalian cells", *Nature*, 411:494-498.

Gautschi, O. et al., (2001), "Activity of a Novel bc1-2/bc1-xL-Bispecific Antisense Oligonucleotide Against Tumors of Diverse Histologic Origins", *Journal of the National Cancer Institute*, 93(6):463-471.

Lipardi, C. et al., (2001), "RNAi as Random Degradative PCR: siRNA Primers Convert mRNA into dsRNAs that Are Degraded to Generate New siRNAs", *Cell*, 107:297-307.

Sharp, P.A., (2001), "RNA interference—2001"; *Genes & Development*, 15:485-490.

Sijen, T. et al., (2001), "On the Role of RNA Amplification in dsRNA-Triggered Gene Silencing", *Cell*, 107:465-476.

Bass, B.L., (2000), "Double-Stranded RNA as a Template for Gene Silencing", *Cell*, 101:235-238.

Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.

Hammond, S.M. et al., (2000), "An RNA-directed nuclease mediates post-transcriptional gene silencing in *Drosophila* cells", *Nature*, 404:293-296.

Yang, D. et al., (2000), "Evidence that processed small dsRNAs may mediate sequence-specific mRNA degradation during RNAi in *Drosophila* embryos", *Current Biology*, 10:1191-1200.

Wianny, F. et al., (2000), "Specific interference with gene function by double-stranded RNA in early mouse development", *Nature Cell Biology*, 2:70-75.

Zamore, P.D. et al., (2000), "RNAi: Double-Stranded RNA Directs the ATP-Dependent Cleavage of mRNA at 21 to 23 Nucleotide Intervals", *Cell*, 101:25-33.

Fire, A., (1999), "RNA-triggered gene silencing", *TIG*, 15(9):358-363.

Tuschl, T. et al., (1999), "Targeted mRNA degradation by double-stranded RNA in vitro", *Genes & Development*, 13:3191-3197.

Wild, K. et al., (1999), "The 2 Å structure of helix 6 of the human signal recognition particle RNA", *Structure*, 7(11):1345-1352.

Montgomery, M.K. et al., (1998), "Double-stranded RNA as a mediator in sequence-specific genetic silencing and co-suppression", *TIG*, 14(7):255-258.

Lowy, D.R. et al., (1993), "Function and Regulation of RAS", *Annu. Rev. Biochem.*, 62:851-891.

Downward, J. et al., (1990), "Identification of a nucleotide exchange-promoting activity for p21$^{ras}$", *Proc. Natl. Acad. Sci. USA*, 87:5998-6002.

Gibbs, J.B. et al., (1988), "Purification of ras GTPase activating protein from bovine brain", *Proc. Natl. Acad. Sci. USA*, 85:5026-5030.

Caplen, N.J., (2002), "A new approach to the inhibition of gene expression", *Trends in Biotechnology*, 20(2):49-51.

Caplen, N.J. et al., (2001), "Specific inhibition of gene expression by small double-stranded RNAs in invertebrate and vertebrate systems", *Proc. Natl. Acad. Sci. USA*, 98(17):9742-9747.

Doench, J.G. et al., (2003), "siRNAs can function as miRNAs", *Genes & Development*, 17:438-442.

Donzé, O. et al., (2002), "RNA interference in mammalian cells using siRNAs synthesized with T7 RNA Polymerase", *Nucleic Acids Research*, 30(10):e46(4pages).

Elbashir, S.M. et al., (2001), "RNA interference is mediated by 21- and 22-nucleotide RNAs", *Genes & Development*, 15:188-200.

Elbashir, S.M. et al., (2001), "Functional anatomy of siRNAs for mediating efficient RNAi in *Drosophila melanogaster* embryo lysate", *The EMBO Journal*, 20(23):6877-6888.

Fire, A. et al., (1998), "Potent and specific genetic interference by double-stranded RNA in *Caenorhabditis elegans*", *Nature*, 391:806-811.

Harborth, J. et al., (2001), "Identification of essential genes in cultured mammalian cells using small interfering RNAs", *Journal of Cell Science*, 114(24):4557-4565.

Lewis, D.L. et al., (2002), "Efficient delivery of siRNA for inhibition of gene expression in postnatal mice", *Nature Genetics*, 32:107-108.

Manche, L. et al., (1992), "Interactions between Double-Stranded RNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ngo, H. et al., (1998), "Double-stranded RNA induces mRNA degradation in *Trypanosoma brucei*", *Proc. Natl. Acad. Sci.*, 95:14687-14692.

Paddison, P.J. et al., (2002), "Short hairpin RNAs (shRNAs) induce sequence-specific silencing in mammalian cells", *Genes & Development*, 16:948-958.

Randall, G. et al., (2003), "Clearance of replicating hepatitis C virus replicon RNAs in cell culture by small interfering RNAs", *PNAS*, 100(1):235-240.

Tijsterman, M. et al., (2002), "The Genetics of RNA Silencing", *Annu. Rev. Genet.*, 36:489-519.

Yu, J. et al., (2002), "RNA interference by expression of short-interfering RNAs and hairpin RNAs in mammalian cells", *PNAS*, 99(9):6047-6052.

Parrish, S. et al. "Functional anatomy of a dsRNA trigger: Differential requirement for the two trigger strands in RNA interference",

*Molecular Cell, Cell Press*, Cambridge, MA, US, vol. 6, No. 5, Nov. 2000, pp. 1077-1087, XP002226298 ISN: 1097-2765.

Fluiter, K. et al., "Tumor Genotype-specific Growth Inhibition in Vivo by Antisense Oligonucleotides against a Polymorphic Site of the Large Subunit of Human RNA Polymerase II," Cancer Research, 62:2024-8 (2002).

Shaw, L. et al., "An allele-specific hammerhead ribozyme gene therapy for a porcine model of autosomal dominant retinitis pigmentosa," Molecular Vision, 7:6-13 (2001).

Shi, M., "Enabling Large-Scale Pharmacogenetic Studies by High-Throughput Mutation Detection and Genotyping Technologies," Clinical Chemistry, 47(2):164-2 (2001).

Hamada M., et al., "Effects on RNA interference in gene expression (RNAi) in cultured mammalian cells of mismatches and the introduction of chemical modifications at the 3'-ends of siRNAs," Antisense & Nucleic Acid Drug Development, Oct. 2002, pp. 301-309, vol. 12, No. 5.

Jacque, J.-M., et al., "Modulation of HIV-1 replication by RNA interference," Nature, Jul. 25, 2002, p. 435-438, vol. 418, No. 6896.

Pasquinelli, A.E., et al., "Conservation of the sequence and temporal expression of let-7 heterochronic regulatory RNA," Nature, Nov. 2, 2000, pp. 86-89, vol. 408, No. 6808.

International Search Report of International Application No. PCT/EP2002/011969, Mar. 13, 2003, 8 Pages.

International Preliminary Examination Report for PCT/EP2002/011969, Mar. 24, 2004, 11 Pages.

International Search Report of International Application No. PCT/EP2002/000151, Jan. 27, 2003, 6 Pages.

Examination Report for European Patent Application No. EP 02779511, Jul. 6, 2009.

Examination Report for European Patent Application No. EP 02779511, Jun. 11, 2008.

* cited by examiner

COMPOSITIONS AND METHODS FOR INHIBITING EXPRESSION OF A MUTANT GENE

RELATED APPLICATIONS

This application is a continuation-in-part of International Application No. PCT/EP02/11969, which designated the United States and was filed on Oct. 25, 2002, which claims the benefit of German Patent No. 101 55 280.7, filed on Oct. 26, 2001, German Patent No. 101 58 411.3, filed on Nov. 29, 2001, German Patent No. 101 60 151.4, filed on Dec. 7, 2001, EP Patent No. PCT/EP02/00152, filed on Jan. 9, 2002, EP Patent No. PCT/EP02/00151, filed on Jan. 9, 2002, and German Patent No. 102 35 620.3, filed on Aug. 2, 2002. The entire teachings of the above applications are incorporated herein by reference.

FIELD OF THE INVENTION

This invention relates to compositions and methods for inhibiting the expression of a mutant gene using double-stranded ribonucleic acid (dsRNA) to mediate RNA interference.

BACKGROUND OF THE INVENTION

Many genetic diseases and defects are caused by only a minor mutation in a specific gene, such as a single-base mismatch (see, e.g., Cooper, D. N., et al., in "*The Metabolic and Molecular Bases of Inherited Disease*" (Scriver, C. R., et al., eds., (McGraw-Hill Inc., New York, Vol. 1, pp. 259-291 (1995)). Due to the high degree of sequence homology, therapeutic agents designed to inhibit the expression of a gene having a single (or multiple) point mutation almost inevitably affects the expression of the normal gene. Treating diseases that result from such genetic aberrations is problematic, particularly in proliferative diseases such as cancer, were expression of the non-mutated gene is essential for normal cellular function.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). When administered to a cell or organism, exogenous dsRNA has been shown to direct the sequence-specific degradation of endogenous messenger RNA (mRNA) through RNAi. This phenomenon has been observed in a variety of organism, including mammals (see, e.g., WO 00/44895, Limmer; and DE 101 00 586 C1, Kruetzer et al.).

While completely complementary dsRNA are robust inhibitors of expression, Elbashir et al. have shown that dsRNA having a three-nucleotide mismatch with the target gene are very poor mediators of RNA interference (Elbashir, S. M., et al., *Nature* (2001) 411:494-498). On the other hand, Holen et al. have shown that dsRNA having one or two nucleotide mismatches can induce RNA interference, thereby inhibiting the expression of the target gene (Holen, T., et al., *Nucl. Acid Res.* (2002) 1757-1766). Thus, there appears to be no clear demarcation in activity upon which to design a dsRNA-based therapeutic agent for treating a disease resulting from a minor genetic aberration. Such an agent would likely produce serious side effects, due to the potential cross-reactivity between the mutant gene and its normal cellular counterpart gene.

While dsRNA can effectively silence a specific target gene, there is currently no available means for selectively inhibiting the expression of a gene comprising a point mutation without also inhibiting the expression of the normal, non-mutated gene. Thus, there remains a need for an agent that can selectively and efficiently silence a mutant gene without also affecting its wild-type counterpart. Compositions comprising such agents would be useful for treating genetic diseases and disorders caused by the expression of a gene having a minor mutation, such as a single or multiple-base mismatch.

SUMMARY OF THE INVENTION

The present invention discloses double-stranded ribonucleic acid (dsRNA), as well as compositions and methods for inhibiting the expression of a target gene having a point mutation(s) using the dsRNA. The present invention also discloses compositions and methods for treating diseases caused by the expression of a mutant gene. The dsRNA of the invention comprises an RNA strand (the complementary strand) having a complementary region that is substantially complementary to an RNA transcript of a target gene having a point mutation, and which is partially complementary to the counterpart, non-mutated cellular gene. More specifically, the complementary region of the dsRNA has at least one base-pair mismatch with the target mutant gene, and at least one more base-pair mismatch with the non-mutated cellular gene.

In one aspect, the invention relates to a double-stranded ribonucleic acid (dsRNA) for selective inhibition of expression of a target mutant gene. The dsRNA comprises a complementary RNA strand and a sense RNA strand, wherein the complementary RNA strand comprises a nucleotide sequence which is substantially complementary to at least a part of the target mutant gene, and partially complementary to at least a part of a corresponding wild-type gene. The complementary nucleotide region may comprise a nucleotide mismatch with the target mutant gene, wherein the mismatch is at least 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides from either end of said nucleotide sequence. The target mutant gene may comprise a point mutation not present in the corresponding wild-type gene. The complementary nucleotide region may have a one-nucleotide sequence mismatch with the target mutant gene, and a two-nucleotide mismatch with the corresponding wild-type gene. The complementary RNA strand and the sense RNA strand may have a nucleotide mismatch. The complementary RNA strand may comprise a 3'-end and a 5'-end, wherein one of the ends has a nucleotide overhang of 1 to 4 nucleotides, preferably 2 or 3 nucleotides in length. The nucleotide overhang is preferably at the 3'-end of the complementary RNA strand, and the 5'-end is blunt. The complementary RNA strand may be 23 nucleotides in length and the sense RNA strand may be 21 nucleotides in length. The complementary RNA strand may be complementary to an RNA transcript of the target mutant gene. The target mutant gene may be an oncogene.

In another aspect, the invention relates to a method for selectively inhibiting the expression of a target mutant gene in a cell. The method comprises introducing into the cell a dsRNA, as described above, and maintaining the cell for a time sufficient to obtain the selective inhibition of expression of the target gene. The complementary RNA strand comprises a nucleotide sequence which is substantially complementary to at least a part of the target mutant gene, and which is partially complementary to at least a part of a corresponding wild-type gene. The target mutant gene may be an oncogene.

In still another aspect, the invention relates to a pharmaceutical composition for selectively inhibiting the expression of a target mutant gene in a mammal. The pharmaceutical composition comprises a dsRNA, as described above, and pharmaceutically acceptable carrier. The dsRNA comprises a complementary RNA strand and a sense RNA strand, wherein the complementary RNA strand comprises a nucleotide sequence which is substantially complementary to at least a part of the target mutant gene, and which is partially complementary to at least a part of a corresponding wild-type gene. The dosage unit of dsRNA may be in a range of 0.01 to 5.0 milligrams, 0.01 to 2.5 milligrams, 0.1 to 200 micrograms, 0.1 to 100 micrograms, 1.0 to 50 micrograms, or preferably 1.0 to 25 micrograms per kilogram body weight of the mammal. The mammal may be a human. The pharmaceutically acceptable carrier may be an aqueous solution, such as a phosphate buffered saline. The pharmaceutically acceptable carrier may comprise a micellar structure, such as a liposome, capsid, capsoid, polymeric nanocapsule, or polymeric microcapsule. The pharmaceutical composition may be formulated to be administered by inhalation, infusion, injection, or orally, preferably by intravenous or intraperitoneal injection.

In yet another aspect, the invention relates to a method for treating a disease caused by the expression of a target mutant gene in a mammal. The method comprises administering to the mammal a pharmaceutical composition comprising a dsRNA and a pharmaceutically acceptable carrier, both of which are described above. The dsRNA comprises a complementary RNA strand and a sense RNA strand, wherein the complementary RNA strand comprises a nucleotide sequence which is substantially complementary to at least a part of the target mutant gene, and also partially complementary to at least a part of a corresponding wild-type gene.

DETAILED DESCRIPTION OF THE INVENTION

The present invention discloses double-stranded ribonucleic acid (dsRNA), as well as compositions and methods for inhibiting the expression of a mutant gene in a cell using the dsRNA. The present invention also discloses pharmaceutical compositions and methods for treating diseases in organisms caused by expression of a gene having at least one point mutation using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the complementary strand) having a complementary region that is substantially complementary to an RNA transcript of the target mutant gene, and which is partially complementary to the counterpart, non-mutated cellular gene. The complementary region of the dsRNA has at least one base-pair mismatch with the target gene, and at least one more base-pair mismatch with its non-mutated counterpart. Using a cell-based assay system, the present inventors have demonstrated the selective inhibition of a target mutant gene (i.e., inhibition of the mutant gene without concomitant inhibition of expression of the corresponding wild-type gene) using a dsRNA comprising at least a two-base pair mismatch with the wild-type gene. Moreover, the inventors have shown a direct relationship between the extent of complementarity between the single strands of the dsRNA and the inhibitory activity of the dsRNA. Thus, one can modify the efficiency of inhibition by altering the degree of complementarity between the two strands of the dsRNA. The present invention encompasses these dsRNAs and compositions comprising dsRNA and their use for specifically silencing genes with point mutations. The use of these dsRNAs enables the targeted degradation of mRNAs of mutated genes that are implicated in a wide variety of disease processes, including cellular proliferative disorders, while minimizing the affect on normal cellular activities. Thus, the methods and compositions of the present invention comprising these dsRNAs are useful for treating diseases and disorders caused by the expression of a mutant gene.

The following detailed description discloses how to make and use the dsRNA and compositions containing dsRNA to inhibit the expression of a target mutant gene, as well as compositions and methods for treating diseases and disorders caused by the expression of the gene. The pharmaceutical compositions of the present invention comprise a dsRNA having a region which is substantially complementary to an RNA transcript of the target mutant gene and which is only partially complementary to the counterpart non-mutated gene, together with a pharmaceutically acceptable carrier. The complementary region of the dsRNA has at least a one base-pair mismatch with the target gene, and at least one more base-pair mismatch with its non-mutated counterpart. Preferably, the complementary strand of the dsRNA is complementary to at least a portion of the 3'-untranslated region of the mRNA. The base-pair mismatch(es) is preferably located at least at least 1 nucleotide, 2 nucleotides, 3 nucleotides, 4 nucleotides, 5 nucleotides, 6 nucleotides, 7, nucleotides, 8 nucleotides, 9 nucleotides, or 10 nucleotides away from either end of the RNA strand.

Accordingly, certain aspects of the present invention relate to pharmaceutical compositions comprising the dsRNA of the present invention together with a pharmaceutically acceptable carrier, methods of using the compositions to inhibit expression of a target mutant gene, and methods of using the pharmaceutical compositions to treat diseases caused by the expression of a gene having a point mutation.

I. DEFINITIONS

For convenience, the meaning of certain terms and phrases used in the specification, examples, and appended claims, are provided below.

As used herein, the terms "target" refers to a section of a DNA strand of a double-stranded DNA that is complementary to a section of a DNA strand, including all transcribed regions, that serves as a matrix for transcription. A target gene, usually the sense strand, is a gene whose expression is to be selectively inhibited or silenced through RNA interference.

As used herein, the terms "mutant gene" and "target mutant gene" refer to a gene comprising at least one point mutation relative to the corresponding normal, non-mutated cellular gene (referred to herein as the "corresponding wild-type gene"). The terms mutant gene and target mutant gene specifically encompass any variant of a normal cellular gene or gene fragment whose expression is associated with a disease or disorder (e.g., an oncogene). Preferably, the target mutant gene has one or two point mutations relative to the corresponding wild-type gene.

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to a region of an mRNA transcript of the target mutant gene (i.e., "the corresponding nucleotide sequence" of the target gene). "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA. The RNA strands may have the same or a different number of nucleotides. The complementary nucleotide region of a complementary RNA strand is less than 25, preferably 19 to 24, more preferably 20 to 24, even more preferably 21 to 23, and most preferably 22 or 23 nucleotides in length. The complementary RNA strand is less than 30, preferably fewer than 25, more preferably 21 to 24, and most preferably 23 nucleotides in length. dsRNAs comprising a complementary or antisense strand of this length (known as "short interfering RNA" or "siRNA") are particularly efficient in inhibiting the expression of the target mutant gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, two polynucleotide sequences are said to be "substantially complementary" to each other when all but one of their respective nucleotides are capable of forming base pairs. The terms "nucleotide mismatch" and "mismatch" refer to a pair of bases that are incapable of forming base-pairs. As used herein, two polynucleotide sequences are said to be "partially complementary" to each other when they have at least one more nucleotide mismatch than their substantially complementary counterparts (i.e., they share at least one fewer base pairs). For example, if polynucleotides A and B are substantially complementary, then polynucleotides A and C are partially complementary if all but at least two of their nucleotides are incapable of forming base pairs. Preferably, the nucleotides that are incapable of forming base pairs are located at least at least 1 nucleotide, 2 nucleotides, 3 nucleotides, 4 nucleotides, 5 nucleotides, 6 nucleotides, 7, nucleotides, 8 nucleotides, 9 nucleotides, or 10 nucleotides away from either end of the nucleotide strand.

As used herein, "selective inhibition of expression" means that a dsRNA has a greater inhibitory effect on the expression of a target mutant gene than on the corresponding wild-type gene. Preferably, the expression level of the target mutant gene is less than 98%, less than 95%, less than 90%, less than 80%, less than 70%, less than 60%, less than 50%, less than 40%, less than 30%, less than 20%, or less than 10% of the expression level of the corresponding wild-type gene.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math*. (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount," or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

II. DOUBLE-STRANDED RIBONUCLEIC ACID (dsRNA)

In one embodiment, the invention relates to a double-stranded ribonucleic acid (dsRNA) having a nucleotide sequence which is substantially identical to at least a portion of a target mutant gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA transcript of the target mutant gene. The dsRNA comprises an RNA strand (the complementary strand) having a complementary region that is substantially complementary to an RNA transcript of the target mutant gene, and which is partially complementary to the counterpart wild-type gene. The complementary region of the dsRNA has at least one base-pair mismatch with the target mutant gene, and at least one more base-pair mismatch with the corresponding non-mutated (wild-type) gene. The dsRNA has less than 30 nucleotides, preferably less than 25 nucleotides, more preferably between 21 and 24 nucleotides, and most preferably 23 nucleotides in length. The dsRNA can be synthesized by standard methods known in the art, e.g., by use of an automated DNA synthesizer, such as are commercially available from Biosearch, Applied Biosystems, Inc.

In one embodiment, the dsRNA is designed to provide a minimal risk of cross-reactivity with normal cellular genes, and thus minimal side effects. In this embodiment, the dsRNA has the maximum number of mismatches between the complementary nucleotide sequence of the complementary RNA strand and the corresponding nucleotide sequence of the target mutant gene that are permissible, while still providing a detectable level of inhibition of expression of the target gene. For example, if one nucleotide mismatch between the complementary nucleotide sequence of the complementary RNA strand and the corresponding nucleotide sequence of the target mutant gene provides optimal inhibition of expression (e.g., 99%), while two and three nucleotide mismatches provide medium and low levels of inhibition of expression (e.g., 60% and 20%), respectively, and four nucleotide mismatches produces no detectable inhibition of expression (0%), then a dsRNA comprising a three-nucleotide mismatch would be chosen. In the other hand, for example, if one nucleotide mismatch between the complementary RNA strand and the target mutant gene provides optimal inhibition of expression (e.g., 95%), while two and three nucleotide mismatches provide low (e.g., 30%) or no detectable inhibition of expression (0%), respectively, then a dsRNA comprising a two-nucleotide mismatch would be chosen. Such levels provide some inhibition of expression of the target gene, and hence some therapeutic value, but with minimal risk of cross-reactivity with the normal cellular genes, and thus minimal side effects. The use of dsRNA having minimal risk of cross-reactivity, albeit sub-optimal efficacy, is particularly advantageous in situations where the side effects are unacceptable or severe.

The present inventors have also discovered that one can improve the efficiency of inhibition by modifying the degree of complementarity between the two RNA strands of the dsRNA. Such a finding is surprising and unexpected, since reducing the level of complementarity between the hybridizing strands typically results in a decrease in stability, thus reducing the effectiveness of inhibition. One of skill in the art may readily determine the degree of mismatching that may be tolerated between any given RNA strands based upon the melting temperature and, therefore, the thermal stability of the resulting duplex. Determination of the appropriate number and location of mismatches for a particular dsRNA can also be made using conventional cell-based assays or on the basis of in vivo testing using an appropriate animal model, as described elsewhere herein.

In another embodiment, at least one end of the dsRNA has a single-stranded nucleotide overhang of between one and four, preferably one or two nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without effecting its overall stability. dsRNA having only one overhang has proven particularly stable and effective in vivo, as well as in a variety of cells, cell culture mediums, blood, and serum. Preferably, the single-stranded overhang is located at the 3'-terminal end of the complementary (antisense) RNA strand or, alternatively, at the 3'-terminal end of the second (sense) strand. The dsRNA may also have a blunt end, preferably located at the 5'-end of the complementary (antisense) strand. Such dsRNAs have improved stability and inhibitory activity, thus allowing administration at low dosages, i.e., less than 5 mg/kg body weight of the recipient per day. The dsRNA may have a blunt end, preferably located at the 5'-end of the complementary (antisense) strand. Preferably, the complementary strand of the dsRNA has a nucleotide overhang at the 3'-end, and the 5'-end is blunt. In another embodiment, one or more of the nucleotides in the overhang is replaced with a nucleoside thiophosphate. In a particularly preferred embodiment, the complementary (antisense) strand is 23 nucleotides in length; the second (sense) strand is 21 nucleotides in length; the 3'-end of the complementary (antisense) RNA strand has a two-nucleotide overhang; and the end of the dsRNA at the 5'-terminal end of the complementary (antisense) strand is smooth.

In an optional embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (e.g., Williams, D. J., and K. B. Hall, *Biochem.* (1996) 35:14665-14670). In a preferred embodiment, the 5'-end of the complementary (antisense) RNA strand and the 3'-end of the second (sense) RNA strand are chemically linked via a hexa-ethylene glycol linker.

III. PHARMACEUTICAL COMPOSITIONS COMPRISING dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression a target mutant gene.

The pharmaceutical compositions of the present invention are administered in dosages sufficient to inhibit expression of the target mutant gene. The present inventors have found that, because of their efficiency, compositions comprising the dsRNA of the invention can be administered at surprisingly low dosages. A maximum dosage of 5 mg dsRNA per kilogram body weight per day is sufficient to inhibit or suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y., *Int. J. Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A. W., et al, *J. Exp. Med.* (1988) 167(2):353-71; Zeng X X et al., *Blood.* (1988) 92(10):3529-36; Eriksson, B., et al., *Exp. Hematol.* (1999) 27(4):682-8; and Kovalchuk, A., et al., *J.* *Exp. Med.* (2000) 192(8): 1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

The present inventors have discovered that there is a direct correlation between the number of complementary nucleotides within the dsRNA (i.e., the number of base pairs between the two complementary RNA strands) and the molecule's inhibitory activity. Reducing the complementarity between the RNA strands of the dsRNA also generally reduces the intracellular or in vivo stability of the dsRNA. Thus, by modifying the number of base pairs within the dsRNA, one can typically adjust the efficiency of inhibition of expression of the target gene.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. METHODS FOR TREATING DISEASES CAUSED BY EXPRESSION OF A TARGET GENE

In one embodiment, the invention relates to a method for treating a subject having a disease or at risk of developing a disease caused by the expression of a target mutant gene. In this embodiment, the dsRNA can act as novel therapeutic agents for controlling one or more of cellular proliferative and/or differentiative disorders. The method comprises administering a pharmaceutical composition of the invention to the patient (e.g., human), such that expression of the target mutant gene is silenced. Because of their high specificity, the dsRNAs of the present invention specifically target mRNAs of mutant genes of diseased cells and tissues, as described elsewhere herein.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoietic origin, e.g., arising from myeloid, lymphoid or erythroid lineages, or precursor cells thereof.

Mutations in cellular genes that directly or indirectly control cell growth and differentiation are considered to be the main cause of cancer. There are approximately thirty families of genes, called oncogenes, that are implicated in human tumor formation. Members of one such family, the RAS gene family, are carried in a broad range of eukaryotes and are frequently found to be mutated in human tumors. Humans carry three functional RAS oncogenes, H-RAS, K-RAS, and N-RAS, coding for 21 kDa proteins 188-189 amino acids long (see, e.g., Lowy & Willumsen, *Annu. Rev. Biochem.* (1993) 2:851-891, 1993). RAS, H-RAS, and N-RAS have been detected in more human tumor types and at higher frequencies than any other oncogenes (Bishop, *Cell* (1991) 64:235-248). In their normal state, proteins produced by the RAS genes are thought to be involved in normal cell growth and maturation. Mutation of the RAS gene, causing an amino acid alteration at one of three critical positions in the protein product, results in conversion to a form that is implicated in tumor formation. Over 90% of pancreatic adenocarcinomas, about 50% of adenomas and adenocarcinomas of the colon, about 50% of adenocarcinomas of the lung, about 50% of carcinomas of the thyroid, about 25% of melanomas, and a large fraction of malignancies of the blood, such as acute myeloid leukemia and myelodysplastic syndrome, have been found to contain activated RAS oncogenes.

Mammalian genes frequently acquire transformation-inducing properties by single point mutations within their coding sequences. Mutations in naturally occurring RAS oncogenes have been localized to codons 12, 13, and 61 (Gibbs, et al., *Proc. Natl. Acad. Sci. USA* (1988) 85:5026-5030). These mutant forms remain in the active GTP form much longer than the wild-type, and presumably, the continual transmission of a signal by the mutant forms is responsible for their oncogenic properties. Reducing the level of K-RAS gene expression might inhibit proliferation or reverse transformation in malignant cells transformed by mutated K-RAS (Georges, et al., *Cancer Res.* 53:1743-1746, 1993; Mukhopadhyay et al., *Cancer Res.* (1991) 51:1744-1748; Kashani-Sabet, et al., *Cancer Res.* (1994) 54:900-902; and Aoki et al., *Cancer Res.* (1995) 55:3810-3815).

In addition to the foregoing oncogenes, the methods and compositions of the invention can be applied to other disease-related target genes having a point mutation. Gene mutations have been reported in more than 1000 different human genes. Data on these mutations and their associated phenotypes have been collated and are available online through two major databases: Online Mendelian Inheritance in Man in Baltimore and the Human Gene Mutation Database in Cardiff. For example, there is a high frequency of CG to TG or CA mutations in the human genome due to deamination of 5' methyl-cytosine. Short deletions or insertions of less than 20 nucleotides are also very common mutations in humans. See, e.g., Antonarakis, S. E., *Eur. J. Pediatr.* (2000) 159(3):S173-8.

Sachidanandam et al. describes a map of human genome sequence variation containing 1.42 million single nucleotide polymorphisms, which is useful for identifying biomedically important genes for diagnosis and therapy (Sachidanandam, R., et al., *Nature* (2001) 409(6822):821-2 and *Nature* (2001) 409(6822):822-3). The map integrates all publicly available SNPs with described genes and other genomic features. An estimated 60,000 SNPs fall within exon (coding and untranslated regions), and 85% of exons are within 5 kb of the nearest SNP. Clifford et al. provides expression-based genetic/physical maps of single-nucleotide polymorphisms identified by the cancer genome anatomy project (Clifford, R., et al., *Genome Res* (2000) 10(8):1259-65). In addition to SNP maps, Sachidanandam et al. provide maps containing SNPs in genes expressed in breast, colon, kidney, liver, lung, or prostate tissue. The integrated maps, a SNP search engine, and a Java-based tool for viewing candidate SNPs in the context of EST assemblies can be accessed via the CGAP-GAI web site http://cgap.nci.nih.gov/GAI/).

The Human Gene Mutation Database (HGMD) represents a comprehensive core collection of data on published germ-line mutations in nuclear genes underlying human inherited disease. The data is publicly available at http://uwcm.ac.uk/uwcm/mg/hgmd0.html. Integration with phenotypic, structural and mapping information are available through links between HGMD and both the Genome Database (GDB) and Online Mendelian Inheritance in Man (OMIM), Baltimore, USA. Hypertext links have also been established to Medline abstracts through Entrez, and to a collection of 458 reference cDNA sequences also used for data checking. See, e.g., Krawczak, M, and D. N. Cooper, *Genet.* (1997) 13(3):121-2; and Cooper, D. N., et al., *Nucleic Acids Res* (1998) 26(1):285-7. Keio Mutation Database (KMDB) is also a database of mutations in human disease-causing genes. These KMDBs are accessible through http://mutview.dmb.med.keio.acjp with advanced internet browsers.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. METHODS FOR INHIBITING EXPRESSION OF A MUTANT GENE

In yet another aspect, the invention relates to a method for inhibiting the expression of a mutant gene in an organism. The method comprises administering a composition of the invention to the organism such that expression of the mutant gene is silenced as compared to the corresponding wild-type gene. The organism may be an animal or a plant. Because of their high specificity, the dsRNAs of the present invention specifically target RNAs (primary or processed) of target mutant genes, and at surprisingly low dosages. Compositions and methods for inhibiting the expression of a target gene using dsRNAs can be performed as described elsewhere herein.

In one embodiment, the invention comprises administering a composition comprising a dsRNA, wherein the dsRNA comprises a nucleotide sequence which is substantially complementary to an RNA transcript of the target mutant gene and partially complementary to the corresponding wild-type gene. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any mutant gene one wishes to silence, thereby selectively inhibiting its expression. Examples of human genes which can be targeted for silencing include, without limitation, an oncogene; cytokinin gene; idiotype protein gene (Id protein gene); prion gene; gene that expresses molecules that induce angiogenesis, adhesion molecules, and cell surface receptors; genes of proteins that are involved in metastasizing and/or invasive processes; genes of proteases as well as of molecules that regulate apoptosis and the cell cycle; and genes that express the EGF receptor; the multi-drug resistance 1 gene (MDR1 gene).

The methods for inhibition the expression of a target mutant gene can also be applied to any plant gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Effect of Complementarity on Inhibition of Expression

In order to make a reporter system, a 26-nucleotide-long sequence of a cDNA sequence that serves as a target gene for the 3'-untranslated region of a corresponding HCV-RNA was fused with the open reading frame of the luciferase gene from the pGL3 expression vector. The pGL3 expression vector came from Promega Co., and is registered under Gene Accession No. U47296 with the National Center for Biotechnology Information(NCBI), National Library of Medicine, Building 38A, Bethesda, Md. 20894. Nucleotides 280 to 1932 were used as the luciferase gene. The 26-nucleotide-long sequence is one that is frequently preserved in many HCV genomes and their subtypes. The 26 nucleotides of the HCV genome that is registered with the NCBI under Gene Accession No. D89815 correspond to Nucleotides 9531 to 9556. They exhibit the following sequence:

5'-gtcacggct agctgtgaaa ggtccgt-3'.  (SEQ ID NO:1)

The resulting fusion gene was cloned as a Bam Hi/Not I DNA fragment in the eukaryote expression plasmid pcDNA 3.1 (+) by Invitrogen GmbH, Karlsruhe Technology Park, Emmy Noether Str. 10, 76131 Karlsruhe, Catalogue No. V790-20. The resulting plasmid was designated p8. The pCMVβGal plasmid from Clontech, Gene Accession No. U 13186, NCBI, that encodes the enzyme β-galactosidase was used as a control for transfection efficiency. The fusion gene plasmid, pCMVβGal, and the various dsRNAs were co-transfected into cells of the liver cell line HuH-7 (JCRB0403, Japanese Collection of Research Bioresources Cell Bank, National Institute of Health Sciences, Kamiyoga 1-18-1, Setagaya-ku, Tokyo 158, Japan). Inhibition of expression of the luciferase gene that was induced by the dsRNAs was determined in relation to the expression of the β-galactosidase gene.

The dsRNAs have the following sequences (designated as SEQ ID NO:2 to SEQ ID NO:13 in the sequence protocol):

HCV1+2, whose S1 strand is completely complementary to the HCV sequence in in the fused HCV-luciferase gene:

```
                                            (SEQ ID NO:2)
S2: 5'-ACG GCU AGC UGU GAA AGG UCC GU-3'

(SEQ ID NO:3)
S1: 3'-AG UGC CGA UCG ACA CUU UCC AGG-5'
```

HCV3+4, which is complementary neither to the HCV- nor to the luciferase sequence in the fused HCV-luciferase gene, and serves as the negative control:

```
                                            (SEQ ID NO:12)
S2: 5'-AGA CAG UCG ACU UCA GCC U GG-3'

(SEQ ID NO:13)
S1: 3'-GG UCU GUC AGC UGA AGU CGG A-5'
```

HCV5+6, whose S1 strand is complementary to the HCV sequence in the fused HCV-luciferase gene, except for the nucleotides that are in bold:

```
                                            (SEQ ID NO:6)
S2: 5'-ACG GCU AGC UGU GAA UGG UCC GU-3'

(SEQ ID NO:7)
S1: 3'-AG UGC CGA UCG ACA CUU ACC AGG-5'
```

HCV7+8, whose S1 strand is complementary to the HCV sequence in the fused HCV-luciferase gene, except for the two nucleotides that are in bold:

```
                                            (SEQ ID NO:8)
S2: 5'-ACG GCA AGC UGU GAA UGG UCC GU-3'

(SEQ ID NO:9)
S1: 3'-AG UGC CGU UCG ACA CUU ACC AGG-5'
```

Luc1+2, whose S1 strand is completely complementary to a luciferase sequence in the fused HCV-luciferase gene, and which serves as the positive control:

```
                                            (SEQ ID NO:10)
S2: 5'-CGU UAU UUA UCG GAG UUG CAG UU-3'

(SEQ D NO:11)
S1: 3'-GC GCA AUA AAU AGC CUC AAC GUC-5'
```

K3s+K3as, which is complementary neither to the HCV- nor to the luciferase sequence in the fused HCV-luciferase gene, and which serves as the negative control:

```
                                            (SEQ ID NO:4)
S2: 5'- G AUG AGG AUC GUU UCG CAU GA-3'

(SEQ ID NO:5)
S1: 3'-UCC UAC UCC UAG CAA AGC GUA -5'
```

HCV5+2, whose S1 strand is completely complementary to the HCV sequence, and whose S2 strand is complementary to the HCV sequence in the fused HCV-luciferase gene, except for the nucleotides that are in bold:

```
                                            (SEQ ID NO:6)
S2: 5'- ACG GCU AGC UGU GAA UGG UCC GU-3'

(SEQ ID NO:3)
S1: 3'-AG UGC CGA UCG ACA CUU UCC AGG -5'
```

HCV1+6, whose S2 strand is completely complementary to the HCV sequence, and whose S1 strand is complementary to the HCV sequence in the fused HCV-luciferase gene, except for the nucleotides that are in bold:

```
                                            (SEQ ID NO:2)
S2: 5'- ACG GCU AGC UGU GAA AGG UCC GU-3'

(SEQ ID NO:7)
S1: 3'-AG UGC CGA UCG ACA CUU ACC AGG -5'
```

HuH-7 cells were cultured in DMEM with 10% FCS. In preparation for transfection, $2\times10^4$ cells were seeded per well of a 96-well cell culture plate. The cells were transfected 24 hours after seeding with 110 µl transfection medium per well total volume. Each transfection was repeated three times. 3 µg of the PCMVβGal plasmid and 1 µg of the p8 plasmid were added to the transfection mixture. The transfection medium contained 0.25 µg of the plasmid mixture per well, and 200, 100, 50, 25, 12.5, or 0 nmol/l of the aforementioned dsRNAs. "Gene Porter 2" from PEQLAB Biotechnology GmbH, Carl Thiersch Str. 2b, 91052 Erlangen, Catalogue No. 13-T202007 was used for the transfection in accordance with manufacturer's instructions. Transfected cells were incubated at 37° C. and 5% $CO_2$. One day after transfection, 35 µl of fresh medium was added per well, and the cells were incubated for another 24 hours. The effect of the dsRNAs was determined by quantifying expressed β-galactosidase with the "Galacto-Star" from Tropix Corp., 47 Wiggins Avenue, Bedford, Mass. 01730, Catalogue No. BM100S, and the effect on the expressed luciferase was determined by chemoluminescence reaction with "Luciferase" from Tropix, Catalogue No. BC100L. The cell lysate was made in accordance with manufacturer's instructions, and 2 µl of it was used per analysis to test for β-galactosidase and 5 µl was used per analysis to test for luciferase. Chemoluminescence measurements were determined using a Sirius Luminometer (Berthold Detection Systems GmbH, Bleichstr. 56-68, 75173 Pforzheim, Germany). The relative activity of luciferase as a measurement of expression was determined by dividing the luciferase value by the β-galactosidase value. An average was then calculated for the three assays. The average for cells transfected without dsRNA was arbitrarily defined as 1.0. The other averages were expressed as a ratio with that value, and these were depicted graphically in FIGS. 1 and 2.

Figure 1:
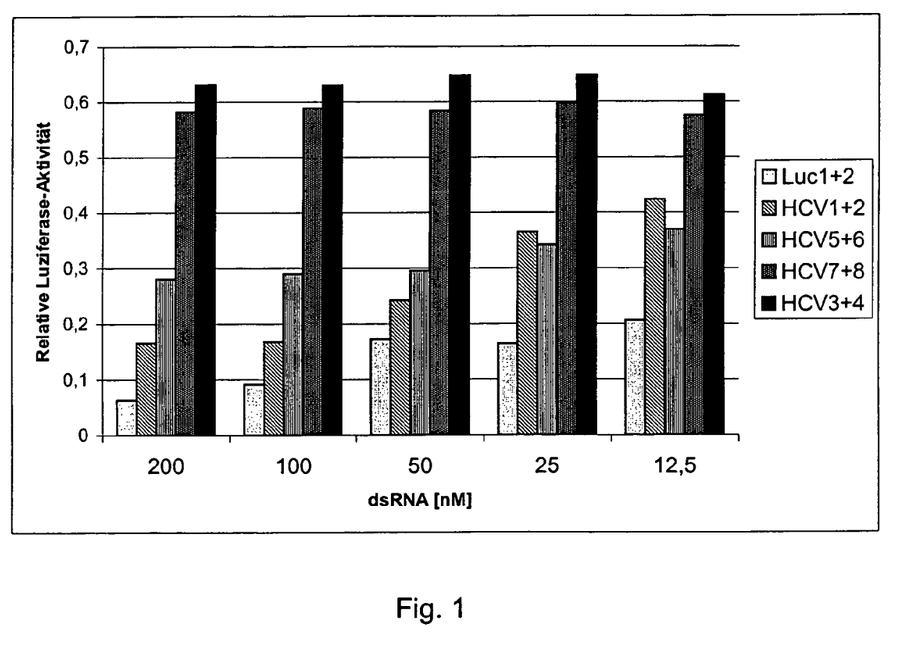
FIG. 1 shows the effect of sequence complementarity on the inhibition of expression of an HCV luciferase fusion protein by dsRNAs.
Figure 2:
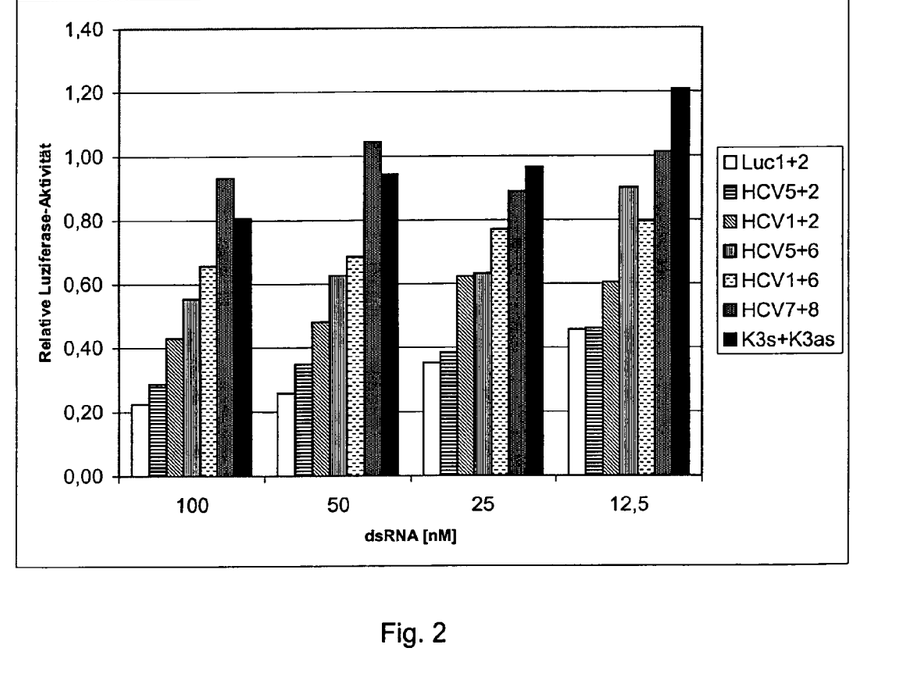
FIG. 2 shows the effect of sequence complementarity, as well as the effect of a single base-pair mismatch between RNA strands of the dsRNA, on the inhibition of expression of an HCV luciferase fusion protein by dsRNAs

Luc 1+2 (positive control) led to the most marked inhibition of luciferase activity (FIGS. 1 and 2). In the presence of HCV1+2, which was completely complementary to the target sequence for the reporter plasmid, a clear reduction in luciferase activity was also discernible (FIGS. 1 and 2). Luciferase activity increased with decreasing concentrations of HCV1+2. The HCV5+6, which is not complementary to the target sequence by one nucleotide, is approximately as effective in inhibiting luciferase as HCV1+2, particularly at low concentrations (FIG. 1).

HCV7+8 inhibits expression of luciferase both at high and at low concentrations only to the same degree as the negative controls HCV3+4 and K3S+K3AS (FIGS. 1 and 2). The scant inhibition of luciferase activity is to be seen as a nonspecific effect. As far as the specificity of this dsRNA is concerned, dsRNA need be either complementary to the target gene, or off by only one nucleotide in order to inhibit expression of the specific target gene as compared to expression of the original gene.

In HCV5+2, one nucleotide in the S2 sense strand is not complementary to the S1 antisense strand, although the S1 antisense strand is completely complementary to the target gene. This dsRNA is as effective as LUC1+2 and HCV1+2 (FIGS. 1 and 2). In HCV6+1, one nucleotide in the S 1 antisense strand is not complementary to the S2 sense strand, while the S1 antisense strand is not complementary to the target gene by one nucleotide. HCV6+1 inhibits expression less effectively than HCV5+6, but more effectively and HCV7+8 (FIG. 2). In other words, specificity and effectiveness of the expression-inhibiting action of dsRNA depends more on the sequence of the S1 antisense strand than on that of the S2 sense strand.

HCV3+4 (FIG. 1) and K3S+K3AS (FIG. 2), which serve as the negative controls, led to no and little inhibition of luciferase activity, respectively. The minor inhibition is nonspecific, as it is not dependent on the dsRNA concentrations used. The data show that at least two nucleotides in the antisense strand of a dsRNA that are not complementary to an original gene are necessary to prevent inhibition of expression of the original gene. Furthermore, the data show that it is possible to modify the effectiveness of inhibition of the expression of the dsRNA by lessening the extent of complementarity of the single strands that form the dsRNA.

Example 2

Treatment of a Colon Cancer Patient with K-Ras siRNA

In this Example, a K-Ras double stranded siRNA directed against K-Ras transcripts with a mutation at codon 12, is injected into colon cancer patients and shown to specifically inhibit K-Ras gene expression.

SiRNA Synthesis siRNAs (K-Ras) directed against mutant K-Ras mRNA are chemically synthesized with or without a hexaethylene glycol linker.

Synthesis and Preparation of dsRNAs

Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 mM $NaClO_4$, pH 6.8, 10% acetonitrile; the high-salt buffer was: 20 mM Tris, 400 mM $NaClO_4$, pH 6.8, 10% acetonitrile. flow rate: 3 ml/min). Formation of double stranded siRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours, In addition, dsRNA molecules with linkers may be produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str. 14, Hamburg, Germany) but with prolonged coupling times. Incorporation of linker phosphoramidite is comparable to the incorporation of nucleoside phosphoramidites.

siRNA Administration and Dosage

The present example provides for pharmaceutical compositions for the treatment of human colon cancer patients comprising a therapeutically effective amount of a K-Ras siRNAs, in combination with a pharmaceutically acceptable carrier or excipient. Examples of suitable carriers are found in standard pharmaceutical texts, e.g. "Remington's Pharmaceutical Sciences", 16th edition, Mack Publishing Company, Easton, Pa., 1980.

The dosage of the siRNAs will vary depending on the form of administration. In the case of an intravenous injection, the therapeutically effective dose of siRNA per injection is in a dosage range of approximately 1-500 microgram/kg body weight per day, preferably at a dose of 100 micrograms/kg/ body weight per day. In addition to the active ingredient, the compositions usually also contain suitable buffers, for example phosphate buffer, to maintain an appropriate pH and sodium chloride, glucose or mannitol to make the solution isotonic. The administering physician will determine the daily dosage which will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The siRNAs of the present invention may be administered alone or with additional siRNA species directed to K-Ras mutant transcripts having other activating point mutations or in combination with other pharmaceuticals.

Efficacy of K-Ras siRNA Treatment

Efficacy of the siRNA treatment is determined at defined intervals after the initiation of treatment using PCR on total RNA extracted from tumor biopsies. Cytoplasmic RNA from the tumor biopsy, taken prior to and during treatment, is purified with the help of the RNeasy Kit (Qiagen, Hilden) and mutant K-Ras mRNA levels are quantitated by RT-PCR (see WO 96/15262 for description of PCR protocol for the detection of mutant K-Ras gene expression).

We claim:

1. A method for inhibiting the expression of a mutant target gene in a mammalian cell in vitro, comprising the steps of:
   a) introducing into said cell in vitro an oligoribonucleotide having a double stranded structure (dsRNA) consisting of two separate non-linked RNA strands,
      wherein a first strand of the dsRNA has a complementary region that is substantially complementary to less than 26 contiguous nucleotides of an RNA transcript of at least part of said target mutant gene and a second strand of the dsRNA is complementary to the first strand, and
   b) maintaining the cell produced in step (a) for a time sufficient to obtain degradation of an RNA transcript of said mutant target gene, thereby inhibiting the expression of said target mutant gene in said cell without inhibiting expression of a wild-type form of the target gene, wherein said first and second strand of said dsRNA are 19 to less than 30 nucleotides in length, and wherein the complementary region of said first strand of said dsRNA contains one mismatch relative to said mutant target gene and at least two mismatches relative to the wild type form of the target gene.

2. The method of claim 1, wherein said first and second strand of said dsRNA are 19 to 24 nucleotides in length.

3. The method of claim 1, wherein the second strand of said dsRNA is from 1 to 4 nucleotides longer than the first strand such that said dsRNA has a 1-4 nucleotide single stranded region at either the 5' or 3' end of said second strand.

4. The method of claim 1, wherein the second strand of said dsRNA is from 1 to 4 nucleotides longer than the first strand such that said dsRNA has a 1-4 nucleotide single stranded region at 3' end of said second strand.

5. The method of claim 1, wherein the second strand of said dsRNA is from 1 to 2 nucleotides longer than the first strand such that said dsRNA has a 1-2 nucleotide single stranded region at either the 5' or 3' end of said second strand.

6. The method of claim 1, wherein the second strand of said dsRNA is from 1 to 2 nucleotides longer than the first strand such that said dsRNA has a 1-2 nucleotide single stranded region at 3' end of said second strand.

7. The method of claim 1, wherein the said mutant gene is an oncogene.

* * * * *

SEQUENCE LISTING

```
<160> NUMBER OF SEQ ID NOS: 13

<210> SEQ ID NO 1
<211> LENGTH: 26
<212> TYPE: DNA
<213> ORGANISM: Hepatitis C virus

<400> SEQUENCE: 1
gtcacggcta gctgtgaaag gtccgt                                         26

<210> SEQ ID NO 2
<211> LENGTH: 23
<212> TYPE: RNA
<213> ORGANISM: Hepatitis C virus

<400> SEQUENCE: 2
acggcuagcu gugaaagguc cgu                                            23

<210> SEQ ID NO 3
<211> LENGTH: 23
<212> TYPE: RNA
<213> ORGANISM: Hepatitis C virus

<400> SEQUENCE: 3
ggaccuuuca cagcuagccg uga                                            23

<210> SEQ ID NO 4
<211> LENGTH: 21
<212> TYPE: RNA
<213> ORGANISM: Artificial sequence
<220> FEATURE:
<223> OTHER INFORMATION: sense strand of a dsRNA that is complementary
      to a sequence of the neomycin resistance gene

<400> SEQUENCE: 4
gaugaggauc guuucgcaug a                                              21

<210> SEQ ID NO 5
<211> LENGTH: 21
<212> TYPE: RNA
<213> ORGANISM: Artificial sequence
<220> FEATURE:
<223> OTHER INFORMATION: antisense strand of a dsRNA that is
      complementary to a sequence of the neomycin resistance gene

<400> SEQUENCE: 5
augcgaaacg auccucaucc u                                              21

<210> SEQ ID NO 6
```

```
<211> LENGTH: 23
<212> TYPE: RNA
<213> ORGANISM: Hepatitis C virus

<400> SEQUENCE: 6
acggcuagcu gugaaugguc cgu                                              23

<210> SEQ ID NO 7
<211> LENGTH: 23
<212> TYPE: RNA
<213> ORGANISM: Hepatitis C virus

<400> SEQUENCE: 7
ggaccauuca cagcuagccg uga                                              23

<210> SEQ ID NO 8
<211> LENGTH: 23
<212> TYPE: RNA
<213> ORGANISM: Hepatitis C virus

<400> SEQUENCE: 8
acggcaagcu gugaaugguc cgu                                              23

<210> SEQ ID NO 9
<211> LENGTH: 23
<212> TYPE: RNA
<213> ORGANISM: Hepatitis C virus

<400> SEQUENCE: 9
ggaccauuca cagcuugccg uga                                              23

<210> SEQ ID NO 10
<211> LENGTH: 23
<212> TYPE: RNA
<213> ORGANISM: Artificial sequence
<220> FEATURE:
<223> OTHER INFORMATION: sense strand of a dsRNA that is complementary
      to a sequence of the luciferase gene

<400> SEQUENCE: 10
cguuauuuau cggaguugca guu                                              23

<210> SEQ ID NO 11
<211> LENGTH: 23
<212> TYPE: RNA
<213> ORGANISM: Artificial sequence
<220> FEATURE:
<223> OTHER INFORMATION: antisense strand of a dsRNA that is
      complementary to a sequence of the luciferase gene

<400> SEQUENCE: 11
cugcaacucc gauaaauaac gcg                                              23

<210> SEQ ID NO 12
<211> LENGTH: 21
<212> TYPE: RNA
<213> ORGANISM: Hepatitis C virus

<400> SEQUENCE: 12
agacagucga cuucagccug g                                                21

<210> SEQ ID NO 13
<211> LENGTH: 21
<212> TYPE: RNA
<213> ORGANISM: Hepatitis C virus
```

```
<400> SEQUENCE: 13
aggcugaagu cgacugucug g                                              21
```